United States Patent [19]

Vince

[11] 4,362,729
[45] Dec. 7, 1982

[54] ALKOXYALKANOATE ESTERS OF CYCLARADINE

[75] Inventor: Robert Vince, St. Paul, Minn.

[73] Assignee: The Regents of the University of Minnesota, Minneapolis, Minn.

[21] Appl. No.: 162,097

[22] Filed: Jun. 23, 1980

[51] Int. Cl.$^3$ .................. C07D 239/70; A61K 31/52
[52] U.S. Cl. ................................ 424/253; 544/277
[58] Field of Search ................ 424/253; 544/264, 277

[56] References Cited

U.S. PATENT DOCUMENTS 4,138,562  2/1979  Vince ............................... 544/264
4,321,376  3/1982  Otani et al. ....................... 424/253

OTHER PUBLICATIONS

Sinkula, Annual Reports Medical Chemistry, vol. 10, pp. 306–315, (ACS), (1975).

Primary Examiner—Nicholas S. Rizzo
Attorney, Agent, or Firm—Burd, Bartz & Gutenkauf

[57] ABSTRACT

Antiviral alkoxyalkanoate esters of cyclaradine having the formula:

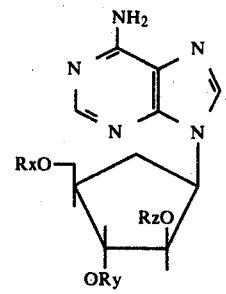

In the monoester Rx is an alkoxyalkanoyl group and Ry and Rz are hydrogen. In the diester Rx and Ry are alkoxyalkanoyl groups and Rz is hydrogen. In the triester Rx, Ry and Rz are alkoxyalkanoyl groups.

12 Claims, 1 Drawing Figure

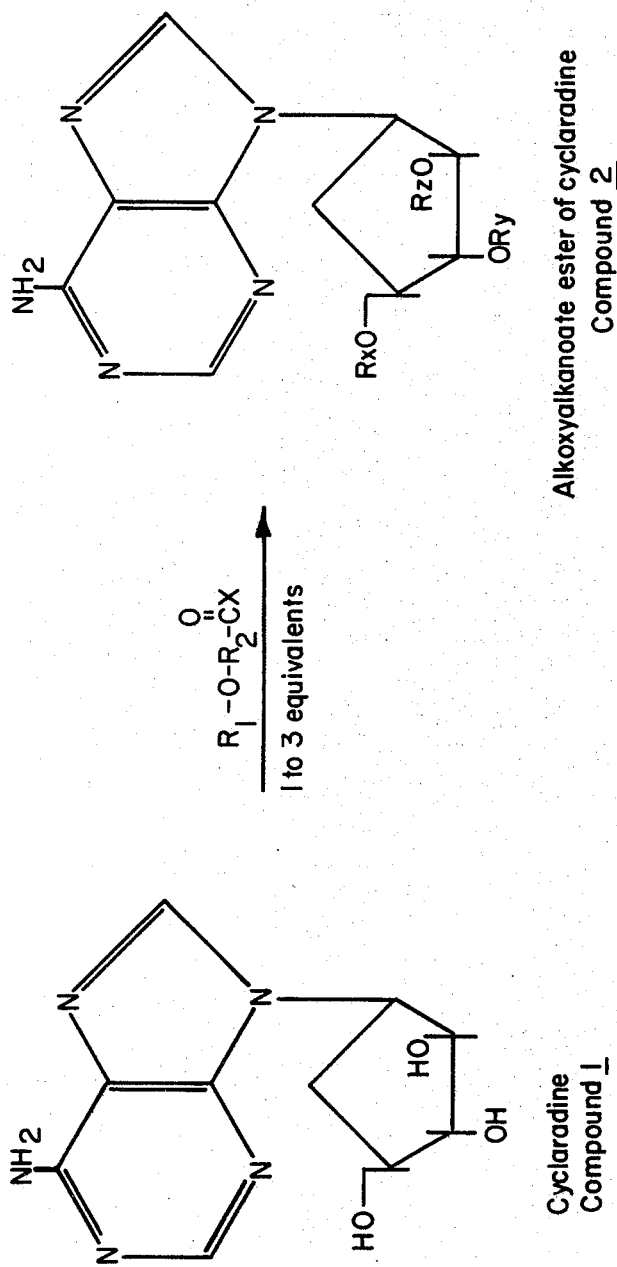
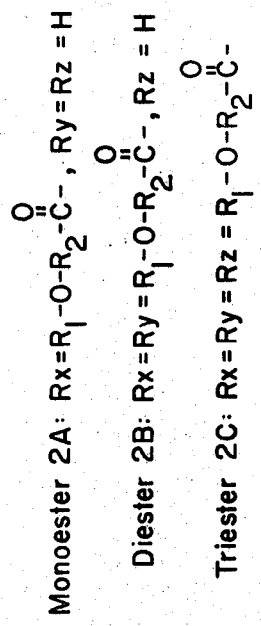
Cyclaradine Compound 1
Alkoxyalkanoate ester of cyclaradine Compound 2
Monoester 2A: $Rx = R_1-O-R_2-\overset{O}{\underset{\|}{C}}-$, $Ry = Rz = H$
Diester 2B: $Rx = Ry = R_1-O-R_2-\overset{O}{\underset{\|}{C}}-$, $Rz = H$
Triester 2C: $Rx = Ry = Rz = R_1-O-R_2-\overset{O}{\underset{\|}{C}}-$
where $R_1$ = lower alkyl having 1-6 carbons
$R_2$ = lower alkyl having 1-6 carbons
$x$ = halogen

ALKOXYALKANOATE ESTERS OF CYCLARADINE

BACKGROUND OF THE INVENTION

1. Field of the Invention

The invention is directed to a small class of esters useful in the treatment of certain viral infections. Additionally, the invention involves topically acceptable formulations of these esters and method of utilizing same.

2. Description of the Prior Art

In U.S. Pat. No. 4,138,562, issued Feb. 6, 1979, and J. Med. Chem., 20, 612 (1977), I disclose the synthesis of the nucleoside 9-[2α,3β-dihydroxy-4α-(hydroxymethyl)cyclopent-1α-yl] which will hereinafter be referred to more simply as C-Ara-A or cyclaradine (Compound 1). Cyclaradine is the parent alcohol of the alkoxyalkanoate esters of this invention. This alcohol and the simple alkanoate esters are the subject of my copending application Ser. No. 1,072, filed Jan. 5, 1979, now U.S. Pat. No. 4,268,672.

Cyclaradine exhibits potent antiviral activity in vitro against viral pathogens such as Herpes and is resistent to the enzyme adenosine deaminase (a normal constituent of human serum) which is responsible for the destruction of the antiviral properties of currently available antiviral nucleosides such as 9-β-D-arabinofuranosyladenine (Ara-A). It has subsequently been found, however, that cyclaradine and its simple alkyl esters are significantly less active in vivo.

SUMMARY OF THE INVENTION

I have now discovered that certain alkoxyalkanoate esters of cyclaradine (Compound 2) exhibit surprisingly greater in vivo activity than the parent alcohols or its simple alkanoate esters. These compounds may be depicted as follows:

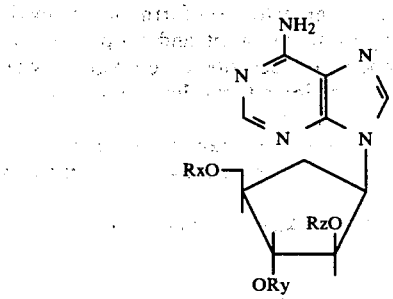

wherein:
in the monoester 2A:

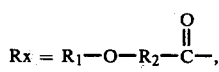

$Ry = Rz = H$,
in the diester 2B:

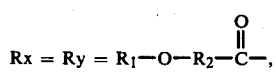

$Rz = H$, or
in the triester 2C:

where
$R_1$ = lower alkyl having 1–6 carbons, and
$R_2$ = lower alkyl having 1–6 carbons.

The monoesters are preferred and in a particularly preferred embodiment Rx is methoxyacetyl and Ry and Rz are hydroxy, i.e. cyclaradine 5'-methoxyacetate.

In addition to significantly increased in vivo activity, these novel alkoxyalkanoate esters also possess the advantage of increased water solubility which greatly facilitates the preparation of suitable cream and other aqueous formulations desirable for administration. The increased water solubility cannot itself explain the enhanced in vivo effectiveness since the simple hydrochloride salt of cyclaradine is highly water soluble, yet is much less effective when applied to the skin than the claimed compounds, or even cyclaradine itself. Moreover, the alkoxyalkanoate esters of this invention are significantly less active in vitro than cyclaradine.

BRIEF DESCRIPTION OF THE DRAWING

The single FIGURE of the accompanying drawing is a flow diagram showing the preparation of the alkoxyalkanoate esters of cyclaradine of the present invention.

DESCRIPTION OF THE PREFERRED EMBODIMENTS

The antiviral compounds 9-[2α,3β-dihydroxy-4α-(hydroxymethyl)cyclopent-1α-yl]adenine alkoxyalkanoate esters 2 are prepared by reaction of cyclaradine 1 with from one to three equivalents of an alkoxyacid halide:

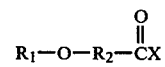

wherein $R_1$ and $R_2$ are lower alkyl groups having from 1 to 6 carbons and X is halogen. Preferably $R_1$ is $CH_3$ and $R_2$ is $-CH_2-$. The alkoxyacid halide is added to a solution of cyclaradine (or an acid salt, such as hydrochloride, thereof) in a non-polar, non-reactive, water-miscible solvent, such as dimethylformamide, dimethylacetamide, tetrahydrofuran, pyridine, or the like. The reaction is carried out at about 4° C. for about 12 to 16 hours with stirring. Water is added to quench the reaction. Volatiles are removed and the ester product is recovered and purified. The monoester results from the reaction of one equivalent of the alkoxyacid halide, the diester from two equivalents, etc.

The invention is illustrated by the following examples:

EXAMPLE 1

9-[2α,3β-dihydroxy-4α(methoxyacetoxymethyl)cyclopent-1α-yl]adenine (2A, where $R_1 = CH_3$, $R_2 = -CH_2-$)

To a solution of cyclaradine 1 (0.106 mole) in dimethylformamide (750 ml) was added methoxyacetyl chloride (0.109 mole) in dimethylformamide (140 ml). The reaction mixture was stirred at 4° C. overnight and then water (50 ml) and sodium bicarbonate (0.27 mole) was added. The volatile materials were removed in vacuo and the residue was applied to a silica gel column. Elution of the major fraction with methanol/chloroform (1.5/10) gave the pure product 2A (60%). Crystallization from methanol/chloroform/hexane and subsequent drying in vacuo at 80° C., m.p. 172°–174° C.

Anal. Calcd for $C_{14}H_{19}N_5O_5$: C, 49.84; H, 5.68; N, 20.76. Found: C, 49.76; H, 5.70; N, 20.83.

Crystallization from water and subsequent drying in vacuo at room temperature gave the dihydrate, m.p. 78°–80° C.

Anal. Calcd for $C_{14}H_{19}N_5O_5.2H_2O$: C, 45.03; H, 6.20; N, 18.75. Found: C, 45.15; H, 6.12; N, 19.00.

EXAMPLE 2

9-[2α-hydroxy, 3β-methoxyacetoxy-4α(methoxyacetoxymethyl)cyclopent-1α-yl]-adenine (2B, where $R_1 = -CH_3$, $R_2 = -CH_2-$)

To a solution of cycloradine 1 (0.106 mole) in dimethylformamide (750 ml) was added methoxyacetylchloride (0.212 mole) in dimethylformamide (140 ml). The reaction mixture was stirred at 4° C. overnight and then water (50 ml) and sodium bicarbonate (0.330 mole) was added. The volatile materials were removed in vacuo and the residue was applied to a silica gel column. The column was eluted with methanol/chloroform (1/10) and the first major fraction was collected and evaporated. Crystallization from ethyl acetate gave 2B as white solid, mp 182°–184° C.

Anal. Calcd for $C_{17}H_{23}N_5O_7$: C, 49.87; H, 5.66; N, 17.11. Found: C, 50.01; H, 5.70; N, 17.26.

EXAMPLE 3

9-[2α,3β-dimethoxyacetoxy-4α(methoxy-acetoxymethyl)cyclopent-1α-yl]adenine (2C, where $R_1 = CH_3$, $R_2 = -CH_2-$)

The triester, 2C, was prepared by the same procedure as described in Example 2, using 0.106 mole of cyclaradine 1 and 0.318 moles of methoxyacetyl chloride.

The compounds of this invention can be used in the treatment of infections caused by DNA-containing viruses such as Herpes virus, including types I and II and Herpes zoster. They can also be used in the treatment of adenoviruses, papovaviruses (warts), picodnaviruses and poxviruses.

The subject alkoxyalkanoate esters can be formulated in standard fashion with conventionally pharmaceutical excipients for topical dosage forms. Such formulations should contain about 1–10% of weight of these esters. For application to the skin, the concentration is desirably in the range of 1–5%, and in a preferred embodiment is 2.5%. Standard dermatological cream and ointment bases can be employed in the usual manner. For treatment of susceptible viral infections of the eye or genital areas, standard ophthalmic and vaginal bases, respectively, such as creams or solutions can be employed.

In a typical regimen, topically acceptable formulations of this invention are applied four times daily to the affected site for a period of five to fourteen days until the infection clears. These compositions can be applied to the infected site in the usual manner. Semi-solid dosage forms can be spread manually or with an applicator, and liquid forms can be applied by dropper or spray.

The following one-gram formulations are exemplary of the products of the invention:

EXAMPLE 4

| 2.5% Topical Cream | |
|---|---|
| cyclaradine 5'-methoxyacetate | 25 mg |
| propylene glycol | 100 mg |
| 4-chloro-m-cresol | 1 mg |
| sodium phosphate, monobasic monohydrate | 2.7 mg |
| phosphoric acid | .02 mg |
| white petrolatum | 150 mg |
| polyethylene glycol monocetyl ether | 18 mg |
| cetostearyl alcohol | 72 mg |
| mineral oil | 60 mg |
| q.s. water, purified U.S.P. | |

Similarly, by increasing the amount of active to 50 mg, a 5% cream is obtained.

EXAMPLE 5

| 2.5% Topical Ointment | |
|---|---|
| cyclaradine 5'-methoxyacetate | 25 mg |
| mineral oil | 50 mg |
| q.s. white petrolatum | |

Similarly, by increasing the amount of active to 50 mg, a 5% ointment is obtained.

EXAMPLE 6

| 2.5% Ophthalmic Ointment | |
|---|---|
| cyclaradine 5'-methoxyacetate | 25 mg |
| methyl paraben | 0.5 mg |
| propyl paraben | 0.1 mg |
| q.s. white petrolatum | |

Similarly, by increasing the amount of active to 50 mg, a 5% ointment is obtained.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. An antiviral alkoxyalkanoate ester of cyclaradine:

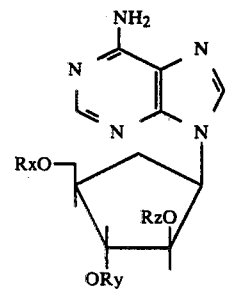

wherein Rx, Ry and Rz are

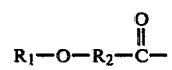

or hydrogen and at least one of Rx, Ry and Rz is

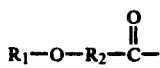

where $R_1$ and $R_2$ are lower alkyl radicals having from 1 to 6 carbons.

2. An alkoxyalkanoate ester according to claim 1 wherein Rx is

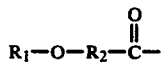

and Ry and Rz are hydrogen.

3. An alkoxyalkanoate ester according to claim 1 wherein Rx and Ry are

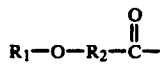

and Rz is hydrogen.

4. An alkoxyalkanoate ester according to claim 1 wherein Rx, Ry and Rz are

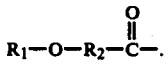

5. An alkoxyalkanoate ester according to claim 1 wherein $R_1$ is $CH_3$ and $R_2$ is —$CH_2$—.

6. An alkoxyalkanoate ester according to claim 5 wherein Rx is

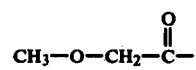

and Ry and Rz are hydrogen.

7. An alkoxyalkanoate ester according to claim 5 wherein Rx and Ry are

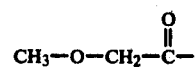

and Rz is hydrogen.

8. An alkoxyalkanoate ester according to claim 5 wherein Rx, Ry and Rz are

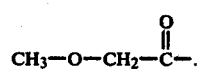

9. Topical antiviral compositions comprising an antivirally effective amount of an alkoxyalkanoate ester of claim 1 in a topically acceptable vehicle.

10. Topical antiviral compositions comprising an antivirally effective amount of an alkoxyalkanoate ester of claim 6 in a topically acceptable vehicle.

11. A method of treating susceptible viral infections comprising applying to the infected area a composition of claim 10.

12. A method of treating susceptible viral infections comprising applying to the infected area a composition of claim 11.

* * * * *